(12) United States Patent
Gatt et al.

(10) Patent No.: US 12,239,964 B2
(45) Date of Patent: Mar. 4, 2025

(54) CATALYSTS AND PROCESSES FOR CONVERTING AROMATICS

(71) Applicant: ExxonMobil Chemical Patents Inc., Baytown, TX (US)

(72) Inventors: Joseph E. Gatt, Annandale, NJ (US); Maryam Peer, Annandale, NJ (US); Natalie A. Fassbender, Nazareth, PA (US); William J. Knaeble, Bridgewater, NJ (US); Jocelyn A. Gilcrest, Mullica Hill, NJ (US); Wenyih F. Lai, Bridgewater, NJ (US); Paul Podsiadlo, Humble, TX (US); Thomas J. Ferro, Bethlehem, PA (US); Doron Levin, Highland Park, NJ (US); Benjamin C. Gamoke, Collingswood, NJ (US)

(73) Assignee: ExxonMobil Engineering & Technology Company, Baytown, TX (US)

( * ) Notice: Subject to any disclaimer, the term of this patent is extended or adjusted under 35 U.S.C. 154(b) by 425 days.

(21) Appl. No.: 17/436,187

(22) PCT Filed: Mar. 26, 2020

(86) PCT No.: PCT/US2020/025025
§ 371 (c)(1),
(2) Date: Sep. 3, 2021

(87) PCT Pub. No.: WO2020/205444
PCT Pub. Date: Oct. 8, 2020

(65) Prior Publication Data
US 2022/0126279 A1 Apr. 28, 2022

Related U.S. Application Data

(60) Provisional application No. 62/826,141, filed on Mar. 29, 2019.

(30) Foreign Application Priority Data

Jul. 9, 2019 (EP) .................................... 19185105

(51) Int. Cl.
*B01J 29/46* (2006.01)
*B01J 35/61* (2024.01)
(Continued)

(52) U.S. Cl.
CPC .............. *B01J 29/46* (2013.01); *B01J 35/613* (2024.01); *B01J 37/0009* (2013.01); *C07C 6/126* (2013.01); *C07C 2529/46* (2013.01)

(58) Field of Classification Search
CPC .. B01J 35/613; B01J 37/0009; B01J 2229/42; B01J 2229/20; B01J 2229/186;
(Continued)

(56) References Cited

U.S. PATENT DOCUMENTS 5,407,880 A 4/1995 Ikeda et al.
5,942,651 A 8/1999 Beech, Jr. et al.
(Continued)

FOREIGN PATENT DOCUMENTS

| EP | 0141514 | | 5/1985 | |
| EP | 0801027 A1 | * | 10/1997 | ............. C01B 39/36 |
| JP | H07155613 | | 6/1995 | |
| WO | WO 2018/071184 | * | 4/2018 | |

*Primary Examiner* — Patricia L. Hailey

(57) ABSTRACT

Methods and corresponding catalysts are provided for conversion of an aromatic feed containing $C_{8+}$ aromatics (particularly $C_{9+}$ aromatics) to form a converted product mixture comprising, e.g., benzene and/or xylenes. The aromatic feed can be converted in the presence of a catalyst that includes a silica binder, a mixture of a first zeolite having an MEL framework (such as ZSM-11 and/or an MFI framework (such as ZSM-5), and a second zeolite having an MOR framework, such as mordenite, particularly a mordenite synthesized using TEA or MTEA as a structure directing (Continued)

agent, and a metal. The catalyst can further include one or more metals supported on the catalyst.

24 Claims, 4 Drawing Sheets

(51) Int. Cl.
    *B01J 37/00*     (2006.01)
    *C07C 6/12*     (2006.01)

(58) Field of Classification Search
CPC . B01J 29/06; B01J 29/185; B01J 29/22; B01J 29/24; B01J 29/26; B01J 29/44; B01J 29/405; B01J 29/46; B01J 29/48; B01J 29/80; Y02P 20/52; C07C 6/126; C07C 2529/46; C07C 2529/22; C07C 2529/44; C07C 2529/80; C07C 15/08
USPC ....... 585/470, 471, 474, 475, 483, 486, 488, 585/489
See application file for complete search history.

(56) References Cited

U.S. PATENT DOCUMENTS

| | | | |
|---|---|---|---|
| 6,559,086 | B1 | 5/2003 | Takahashi et al. |
| 6,867,340 | B2 | 3/2005 | Oh et al. |
| 7,626,064 | B1 | 12/2009 | Boldingh et al. |
| 7,663,010 | B2 | 2/2010 | Levin |
| 8,163,966 | B2 | 4/2012 | Levin |
| 8,183,424 | B2 | 5/2012 | Levin et al. |
| 8,481,443 | B2 | 7/2013 | Levin et al. |
| 9,006,125 | B2 | 4/2015 | Levin et al. |
| 9,034,780 | B2 | 5/2015 | Levin |
| 10,053,403 | B2 | 8/2018 | Lai et al. |
| 10,058,853 | B2 | 8/2018 | Lai et al. |
| 10,118,165 | B2 | 11/2018 | Lai et al. |
| 10,669,491 | B2 | 6/2020 | McCarthy et al. |
| 2015/0217281 | A1 | 8/2015 | Berg-Slot et al. |
| 2018/0029025 | A1 | 2/2018 | Elia et al. |
| 2018/0134637 | A1 | 5/2018 | Lai et al. |
| 2019/0359542 | A1 | 11/2019 | Detjen et al. |
| 2020/0031740 | A1* | 1/2020 | Elias .................... B01J 29/7492 |
| 2022/0126278 | A1 | 4/2022 | Peer et al. |

* cited by examiner

CATALYSTS AND PROCESSES FOR CONVERTING AROMATICS

CROSS-REFERENCE TO RELATED APPLICATIONS

This application is a US national phase application of PCT Application Serial No. PCT/US2020/025025 having a filing date of Mar. 26, 2020, which claims priority to and the benefit of U.S. Provisional Application No. 62/826,141 having a filing date of Mar. 29, 2019 and European Patent Application No. 19185105.4 having a filing date of Jul. 9, 2019, the disclosures of all of which are incorporated herein by reference in their entireties.

FIELD

Catalysts and corresponding catalytic methods are provided for conversion of aromatic hydrocarbons to more valuable products, such as transalkylation of heavy aromatics to make xylenes.

BACKGROUND

One source of benzene and xylenes is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains BTX (benzene, toluene, and xylenes), along with ethylbenzene.

Refineries have also focused on the production of benzene and xylenes by transalkylation of lower value $C_9+$ aromatics with benzene or toluene to produce xylenes as increasingly important process. Chemical plants would ideally like to process as much of the heavy $C_9+$ aromatics as possible while minimizing and potentially removing the toluene/benzene co-feed. Both transalkylation activity and dealkylation activity are important for a successful catalyst system. Transalkylation is the ability to transalkylate methyl groups to form xylenes. Dealkylation activity is the ability to dealkylate ethyl and propyl groups present on the $C_9+$ aromatics to allow the formation of lower methyl/ring species that may transalkylate with higher methyl/ring species to form xylenes. Metal function is required to saturate olefins formed during dealkylation while maintaining the integrity of the aromatic saturations. As plants move to increased amounts of $C_9+$ in the feed, acceptable activity and catalyst life become challenging.

A catalyst system for the transalkylation of $C_{9+}$ aromatics with $C_6$-$C_7$ aromatics is disclosed in U.S. Pat. No. 7,663,010. The catalyst system described therein comprises (a) a first catalyst comprising a molecular sieve having a Constraint Index in the range of 3-12 (e.g., a 10 MR molecular sieve, such as ZSM-5, ZSM-11, ZSM-22, and ZSM-23) and a metal catalyzing the saturation of the olefins formed by the dealkylation reactions and (b) a second catalyst comprising a molecular sieve having a Constraint Index in the range of less than 3 (e.g., a 12 MR molecular sieve, such as ZSM-12, MOR, zeolite beta, MCM-22 family molecular sieve) and optionally a metal which may be the same or different to the metal on the first catalyst. U.S. Pat. Nos. 8,163,966 and 9,034,780 describe additional catalyst systems and methods for performing transalkylation on mixed aromatic feeds.

U.S. Pat. Nos. 8,183,424, 8,481,443, and 9,006,125 discloses improved performance with a stacked bed system in a process for producing xylene by transalkylation of a $C_9+$ aromatic hydrocarbon feedstock contacted with a $C_6$ and/or $C_7$ aromatic hydrocarbon and hydrogen with a first catalyst comprising (i) a first molecular sieve having a Constraint Index in the range of 3 to 12 and (ii) at least first and second different metals or compounds thereof of Groups 6 to 12 of the IUPAC Periodic Table of the Elements under conditions effective to dealkylate aromatic hydrocarbons and to saturate $C_2+$ olefins formed so as to produce a first effluent. At least a portion of the first effluent is then contacted with a second catalyst comprising a second molecular sieve having a Constraint Index less than 3 under conditions effective to transalkylate $C_9+$ aromatic hydrocarbons with said $C_6/C_7$ aromatic hydrocarbon to form a second effluent comprising xylene.

U.S. Pat. No. 10,118,165 describes catalyst compositions and their use in heavy aromatics conversion processes. The catalyst compositions include a mixture of a first zeolite having a Constraint Index of 3 to 12, a second zeolite corresponding to a mordenite zeolite synthesized from tetraethylammonium cation (TEA) or methyl tetraethylammonium cation (MTEA), a Group 10 metal, and a Group 11-15 metal. Examples of the zeolite including a constraint index of 3 to 12 include ZSM-5 and ZSM-11.

SUMMARY

It has been found, in a surprising manner, that a catalyst composition comprising a mixture of a MEL framework first zeolite such as ZSM-11, a MOR framework second zeolite such as mordenite, and optionally a third MFI zeolite such as ZSM-5, a metal such as Pt, and a silica binder, demonstrated superior performance over similar catalyst compositions free of a MEL framework zeolite, but comprising alternative zeolite such as ZSM-5 in lieu thereof, in terms of one or more of at least aromatic selectivity, ethyl-substituted aromatics, xylene yield, and aging rate in aromatic conversion processes such as transalkylation of $C_{9+}$ aromatics with benzene/toluene.

In a first aspect, this disclosure relates to a method for converting a feedstock comprising $C_{8+}$ aromatics, the method comprising: contacting the feedstock and optionally hydrogen with a catalyst composition under conversion conditions in a reactor comprising at least one fixed catalyst bed of the catalyst composition to produce a converted product mixture, wherein the catalyst composition comprises: (i) a zeolite mixture comprising a first zeolite selected from MEL framework zeolites, MFI framework zeolites, and mixtures and combinations of two or more thereof, and a second zeolite having a MOR framework; (ii) a combination of a first metal in Groups 7-10 and a second metal in Groups 2, and 11 to 15 in the Periodic Table of Elements; and (iii) a silica binder.

In a second aspect, this disclosure relates to a catalyst composition comprising: (i) a zeolite mixture comprising a first zeolite selected from MEL framework zeolites, MFI framework zeolites, and mixtures and combinations of two or more thereof, and a second zeolite having a MOR framework; (ii) a combination of a first metal in Groups 7-10 and a second metal in Groups 2, and 11 to 15 in the Periodic Table of Elements; and (iii) a silica binder.

DETAILED DESCRIPTION

Overview

Figure 1:
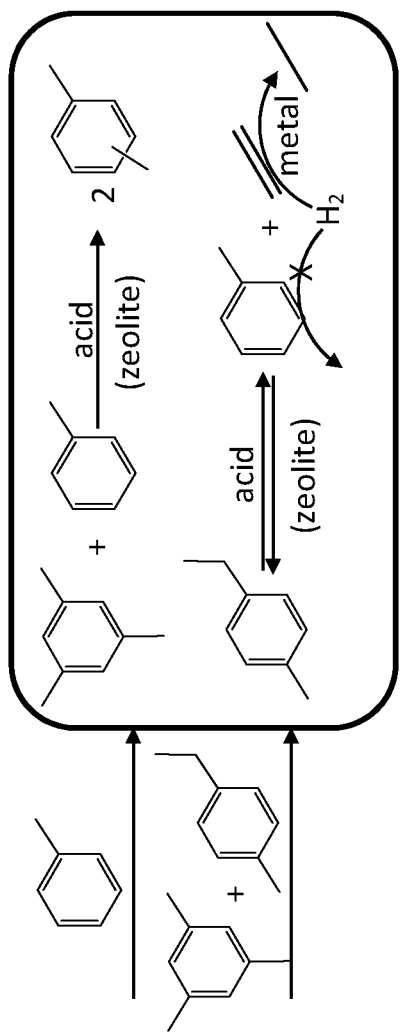
FIG. 1 shows various reaction pathways that can be present during conversion of a heavy aromatic feed.

In various aspects and embodiments, methods and corresponding catalysts are provided for conversion of an aromatic feed containing $C_{8+}$ aromatics (especially heavy aromatics containing $C_{9+}$ aromatics) to form benzene and/or xylenes. The aromatic feed can be converted in the presence of a catalyst that includes a silica binder and a mixture of a first zeolite having a MEL framework (such as ZSM-11) and/or a MFI framework (such as ZSM-5), a second zeolite having a MOR framework, such as mordenite, particularly mordenite synthesized using TEA or MTEA as a structure directing agent. The catalyst can further include one or more metals supported on the catalyst.

It has been discovered that silica-bound catalysts including a mixture of i) a MEL zeolite, or a MFI zeolite, or a mixture of MEL zeolite and MFI zeolite with desirable weight ratio therebetween and (ii) a MOR framework zeolite (e.g., mordenite, particularly mordenite synthesized using TEA or MTEA) can provide an unexpectedly beneficial combination of properties. For example, it has been discovered that use of a silica binder can unexpectedly reduce or minimize the aging rate of catalyst including a mixture of i) MEL and/or MFI framework zeolite and ii) mordenite (particularly mordenite synthesized using TEA or MTEA). This can facilitate the use, for example, of MEL and/or MFI framework zeolite with a higher silica to alumina ratio while providing improved catalyst lifetime. Such a catalyst having a silica binder can also allow for simplified catalyst activation and start-up, due in part to a lower differential between the catalyst activity for fresh catalyst and the catalyst activity after a small amount of exposure to feedstock.

Additionally or alternately, the aromatic selectivity of such a catalyst having a silica binder can be unexpectedly high relative to the amount of conversion of ethyl-substituted aromatics, while also providing an improved yield of xylenes. Ethyl-substituted aromatics, such as ethylbenzene, are less desirable components in a product mixture including xylenes, due in part to the difficulty in separating such ethyl-substituted aromatics from other desired products. However, conversion of ethyl-substituted aromatics by saturation and/or opening of the aromatic ring represents a net loss of potential product, as such saturated and/or opened aromatic rings can no longer be recycled easily for production of additional desired aromatic products. Thus, the ability to reduce or minimize aromatic loss (i.e., high aromatic selectivity) while also providing increased amounts of conversion of ethyl-substituted aromatics is beneficial for commercial production of aromatic products, such as benzene, toluene, and/or xylenes.

It has further been discovered that use of a silica binder can unexpectedly reduce or minimize the aging rate of catalyst including a mixture of MEL framework zeolite and mordenite synthesized using TEA or MTEA. This can facilitate the use, for example, of MEL framework zeolite with a higher silica to alumina ratio while providing improved catalyst lifetime.

Conversion of an aromatic feed including $C_{8+}$ (particularly $C_{9+}$) aromatics can require balancing of a variety of reaction mechanisms to achieve a desired product. FIG. 1 shows an overview of several exemplary reactions that can occur during a transalkylation process between toluene and $C_9$ aromatics (represented by 1,3,5-tri-methylbenzene and 1-methyl-4-ethylbenzene, two exemplary $C_9$ aromatic hydrocarbons) in a transalkylation reactor. One desirable reaction is the transalkylation between the $C_9$ aromatic hydrocarbons (e.g., 1,3,5-trimethylbenzene) with toluene to produce highly valuable xylenes catalyzed by an acid such as a zeolite. Another desirable reaction is the de-ethylation of ethyl-containing aromatic hydrocarbons (e.g., 1-methyl-4-ethyl-benzene) to form toluene/benzene and an olefin (e.g.) ethylene in the presence of an acid such as a zeolite. It is highly desirable that the olefin (ethylene) is hydrogenated to ethane in the presence of hydrogenation metal catalyst to prevent it from ethylating an aromatic compound. On the other hand, it would be highly undesirable to allow the aromatics (e.g., toluene) to undergo hydrogenation in the presence of the hydrogenation metal catalyst to form non-aromatic species, resulting in loss of aromatic rings ("ring loss"). The aromatic compounds, including benzene, toluene, xylenes, and the like, are considered high-value molecules than the non-aromatic hydrocarbons. Thus, it would be highly desirable to reduce ring loss and to increase de-ethylation in an aromatic conversion process such as a transalkylation process. The ability to balance the group of reactions shown in FIG. 1 is of high value commercially, as the ability to selectivity remove ethyl-substituted aromatics while reducing or minimizing loss of aromatic rings can allow for increased net yield from conversion of the feed while simplifying the separation processes that are needed to isolate xylenes from other components of the conversion effluent.

Conventionally, some types of catalysts or catalysts systems for conversion of an aromatic effluent (particularly those containing $C_{9+}$ aromatics) can involve using some combination of mordenite, a zeolite such as ZSM-5, and a combination of Pt with another metal supported on the catalyst. For catalysts include mordenite and ZSM-5, use of a combination of Pt with Sn can appear to be less favorable in comparison with a combination of Pt with Ga. This is due in part to lower activity for catalysts including a combination of Pt and Sn for conversion of ethyl-substituted aromatics. However, it has been discovered that when using a combination of ZSM-11 and mordenite, a combination of Pt and Sn as catalytic metals can provide an unexpectedly beneficial combination of aromatic selectivity (i.e., preserving aromatic rings in the conversion effluent) for a given or target level of conversion of ethyl-substituted aromatics.

As used in this specification, the term "framework type" is used in the sense described in the "Atlas of Zeolite Framework Types," 2001.

The term "aromatic" as used herein is to be understood in accordance with its art-recognized scope which includes alkyl substituted and unsubstituted mono- and polynuclear compounds. The term "ethyl-substituted aromatic" refers to aromatics such as ethylbenzene that include at least one ethyl group as a substituent of the aromatic ring.

The term "hydrocarbon" means (i) any compound consisting of hydrogen and carbon atoms or (ii) any mixture of two or more such compounds in (i). The term "$C_n$ hydrocarbon," where n is a positive integer, means (i) any hydrocarbon compound comprising carbon atom(s) in its molecule at the total number of n, or (ii) any mixture of two or more such hydrocarbon compounds in (i). Thus, a $C_2$ hydrocarbon can be ethane, ethylene, acetylene, or mixtures of at least two of them at any proportion. A "$C_m$ to $C_n$ hydrocarbon" or "$C_m$-$C_n$ hydrocarbon," where m and n are positive integers and m<n, means any of Cm, Cm+1, Cm+2, ..., Cn−1, Cn hydrocarbons, or any mixtures of two or more thereof. Thus, a "$C_2$ to $C_3$ hydrocarbon" or "$C_2$-$C_3$ hydrocarbon" can be any of ethane, ethylene, acetylene, propane, propene, propyne, propadiene, cyclopropane, and any mixtures of two or more thereof at any proportion between and among the components. A "saturated $C_2$-$C_3$ hydrocarbon" can be ethane, propane, cyclopropane, or any mixture thereof of two or more thereof at any proportion. A "$C_{n+}$ hydrocarbon" means (i) any hydrocarbon compound comprising carbon atom(s) in its molecule at the total number of at least n, or (ii) any mixture of two or more such hydrocarbon compounds in (i). A "$C_{n-}$ hydrocarbon" means (i) any hydrocarbon compound comprising carbon atoms in its molecule at the total number of at most n, or (ii) any mixture of two or more such hydrocarbon compounds in (i). A "$C_m$ hydrocarbon stream" means a hydrocarbon stream consisting essentially of $C_m$ hydrocarbon(s). A "$C_m$-$C_n$ hydrocarbon stream" means a hydrocarbon stream consisting essentially of $C_m$-$C_n$ hydrocarbon(s).

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure. Additionally, they do not exclude impurities and variances normally associated with the elements and materials used. "Consisting essentially of" a component in this disclosure can mean, e.g., comprising, by weight, at least 80 wt %, of the given material, based on the total weight of the composition comprising the component.

In this discussion, references to groups of elements correspond to groups according to the IUPAC Periodic Table. Thus, Group 10 metals include Ni, Pt, and Pd.

As used herein, the term "meso-mordenite" means a mordenite zeolite having a mesopore surface area of greater than 30 m²/g. Said meso-mordenite zeolite can be synthesized from TEA or MTEA, and may comprise agglomerates composed of primary crystallites, wherein said primary crystallites have an average primary crystal size as measured by TEM of less than 80 nm and an aspect ratio of less than 2, as disclosed in U.S. Pat. No. 10,017,394, which is incorporated by reference herein.

As used herein, the term "medium pore zeolite" means a zeolite having a constraint index of 3 to 12. As used herein, the term "constraint index" is defined in U.S. Pat. Nos. 3,972,832 and 4,016,218, both of which are incorporated herein by reference.

As used herein, the term "TEA" means tetraethylammonium cation. As used herein, the term "MTEA" means methyltriethylammonium cation. The term "aspect ratio" when used in reference to the primary crystals is defined as the longest dimension of the crystallite divided by the width of the crystallite, where the width of the crystallite is defined as the dimension of the crystallite in the middle of that longest dimension in a direction orthogonal to that longest dimension, as measured by TEM, is relatively low, for example, less than 2.0. Typically, the primary crystals are not elongated crystals having an aspect ratio greater than 2.0, or platelets.

As used herein, the term "primary crystal" denotes a single, indivisible crystal in contrast to an agglomerate. Primary crystals typically adhere together through weak physical interactions (rather than chemical bonds) to form agglomerates. The words "crystal" and "crystallite" are used herein interchangeably.

Catalyst Composition

The catalyst composition employed in the process of the invention comprises a silica binder a first zeolite having an MEL framework type and/or an MFI framework type, a second zeolite comprising a MOR framework zeolite (e.g., mordenite, particularly mordenite zeolite synthesized from TEA or MTEA), at least one first metal of Group 10, and at least one second metal of Group 11 to 15 of the IUPAC Periodic Table, wherein the MOR framework zeolite can be a meso-porous zeolite having a mesopore surface area of greater than 30 m²/g. The MOR framework zeolite can comprise agglomerates composed of primary crystallites, and wherein the primary crystallites have an average primary crystal size as measured by TEM of less than 80 nm and an aspect ratio of less than 2. Preferably, the Group 10 metal can be Pt and the Group 11 to 15 metal can be Sn. The MOR framework zeolite can be a meso-mordenite.

ZSM-11 is an example of an MEL framework type zeolite. ZSM-11 has a constraint index of 3 to 12. ZSM-11 is described in U.S. Pat. No. 3,709,979, which is incorporated herein by reference. Constraint index and a method for its determination are described in U.S. Pat. No. 4,016,218, which is incorporated herein by reference with regard to the description of constraint index and the method of its determination. Preferably the first zeolite consists essentially of ZSM-11, e.g., comprising ZSM-11 at a concentration of at least, e.g., 85, 90, 95, 98, 99, or even 100 wt %, based on the total weight of the first zeolite.

Another example of MEL framework type zeolite is SSZ-46 (described in U.S. Pat. No. 5,968,474), TS-2 (described in Reddy, J. S. and Kumar, R., Crystallization kinetics of a new titanium silicate with MEL structure (TS-2), *Zeolites,* 12, 95-100 (1992), which can be useful in the first zeolite of the zeolite mixture of the catalyst composition of this disclosure. The contents of these references are incorporated by reference in their entirety. These alternative MEL framework zeolites, and ZSM-11, can be used alone or in combination in or as the first zeolite.

The second zeolite comprises a MOR framework zeolite, such as mordenite, particularly mordenite synthesized from TEA or MTEA structure directing agents. It is desirable that the MOR framework zeolite has a mesopore surface area of greater than 30 m²/g. The MOR framework zeolite can comprise agglomerates of primary crystallites, wherein said primary crystallites have an average primary crystal size as measured by TEM (transmission electron microscopy) of less than 80 nm and an aspect ratio of less than 2. Preferably the second zeolite consists essentially of mordenite, e.g., comprising mordenite at a concentration of at least, e.g., 85, 90, 95, 98, 99, or even 100 wt %, based on the total weight of the second zeolite. Preferably the second zeolite consists essentially of meso-mordenite, e.g., comprising meso-mordenite at a concentration of at least, e.g., 85, 90, 95, 98, 99, or even 100 wt %, based on the total weight of the second zeolite.

Other examples of zeolites having an MOR framework include: RMA-1 (described in Itabashi, K., Matsumoto, A., Ikeda, T., Kato, M. and Tsutsumi, K., Synthesis and characteristic properties of Rb-mordenite, *Microporous Mesoporous Mat.,* 101, 57-65 (2007)); Ga—Si—O-MOR, described in Eapen, M. J., Reddy, K. S. N., Joshi, P. N. and Shiralkar, V. P., Synthesis of a Gallosilicate Analogue of High Silica, Large Port Mordenite, *J. Incl. Phenom.,* 14, 119-129 (1992); LZ-211 (described in U.S. Pat. No. 4,503, 023); Large-port and small port mordenites described in Sand, L. B., Synthesis of large-port and small-port mordenites, *Molecular Sieves*, pp. 71-77 (1968). The contents of all these references are hereby incorporated by reference in their entirety. These MOR framework type zeolites, together with ZSM-11, maybe used alone or in combination in the second zeolite of the catalyst composition of this disclosure.

The meso-mordenite zeolite can comprise agglomerates, typically irregular agglomerates. The agglomerates are composed of primary crystallites which have an average primary crystal size as measured by TEM of less than 80 nm, preferably less than 70 nm and more preferably less than 60 nm, for example, less than 50 nm. The primary crystallites may have an average primary crystal size as measured by TEM of, for example, greater than 20 nm, optionally greater than 30 nm.

Optionally, the primary crystals of the meso-mordenite zeolite have an average primary crystal size of less than 80 nm, preferably less than 70 nm, and in some cases less than 60 nm, in each of the a, b and c crystal vectors as measured by X-ray diffraction. The primary crystallites may optionally have an average primary crystal size of greater than 20 nm, optionally greater than 30 nm, in each of the a, b and c crystal vectors, as measured by X-ray diffraction.

The meso-mordenite zeolite will generally comprise a mixture of agglomerates of the primary crystals together with some unagglomerated primary crystals. The majority of the meso-mordenite zeolite, for example, greater than 80 weight % or greater than 90 weight % will be present as agglomerates of primary crystals. The agglomerates are typically of irregular form. For more information on agglomerates please see Walter, D. (2013) Primary Particles—Agglomerates—Aggregates, in Nanomaterials (ed. Deutsche Forschungsgemeinschaft (DFG)), Wiley-VCH Verlag GmbH & Co. KGaA, Weinheim, Germany doi: 10.1002/9783527673919, pages 1-24. Usefully, the meso-mordenite zeolite is not an aggregate.

Optionally, the meso-mordenite zeolite comprises at least 50% by weight, preferably at least 70% by weight, advantageously at least 80% by weight, more preferably at least 90% by weight and optionally substantially consists of said irregular agglomerates composed of primary crystallites having a primary crystal size of less than 80 nm, preferably less than 70 nm, and more preferably less than 60 nm, for example, less than 50 nm Preferably, the meso-mordenite zeolite of the invention comprises less than 10% by weight of primary crystallites having a size of more than 80 nm as assessed by TEM. Preferably, the meso-mordenite zeolite of the invention is composed of said irregular agglomerates composed of crystallites having a crystal size as measured by TEM of less than 80 nm. Preferably, the meso-mordenite zeolite of the invention is substantially free, for example, contains less than 10% by number as assessed by TEM, of needle or platelet crystals.

Preferably, said primary crystallites of the meso-mordenite zeolite of the invention have an aspect ratio of less than 3.0, more preferably less than 2.0, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM.

Said agglomerates of said primary crystallites are typically of irregular form and may be referred to as being "secondary" particles because they are formed of agglomerates of the crystallites, which are the "primary" particles.

The primary crystallites may have a narrow particle size distribution such that at least 90% of the primary crystallites by number have a primary crystal size in the range of from 20 to 80 nm, preferably in the range of from 20 to 60 nm, as measured by TEM.

The meso-mordenite has a very small crystal size and a high mesopore surface area, in particular by the selection of the synthesis mixture composition. The very small primary crystal size promotes access of reactant compounds to the active sites within the pores of the mordenite, thereby increasing catalytic efficiency.

The meso-mordenite zeolite has a mesopore surface area as measured by BET of greater than 30 m$^2$/g, preferably greater than 40 m$^2$/g, and in some cases greater than 45 m$^2$/g.

The meso-mordenite zeolite preferably has a total surface area of greater than 500 m$^2$/g, more preferably greater than 550 m$^2$/g, and in some cases greater than 600 m$^2$/g. The total surface area includes the surface area of the internal pores (zeolite surface area) and also the surface area on the outside of the crystals (the external surface area). The total surface area is measured by BET.

Preferably, the ratio of the meso-mesopore surface area to the total surface area for the meso-mordenite zeolite is greater than 0.05.

The meso-mordenite zeolite preferably has a mesopore volume of greater than 0.1 mL/g, more preferably greater than 0.12 mL/g, and in some cases greater than 0.15 mL/g.

The Si:Al$_2$ (or SiO$_2$/Al$_2$O$_3$) molar ratio of the meso-mordenite zeolite of the invention is preferably greater than 10 and may be in the range of, for example, from 10 to 60, preferably from 15 to 40. The ratio Si:Al$_2$ of the post-treated mordenite zeolite is preferably in the range of from 40 to 300, more preferably from 60 to 150.

The meso-mordenite zeolite may be prepared by the method comprising the steps of:

a) providing a synthesis mixture comprising a silicon source, an aluminum source, an alkali metal (M) hydroxide, a source of a structure directing agent (SDA) selected from the group consisting of tetraethylammonium cation (TEA), methyltriethylammonium cation (MTEA) and mixtures thereof, optional seed crystals and water, said synthesis mixture having a composition including the following molar ratios:

SiO$_2$: Al$_2$O$_3$ 15-40
OH$^-$: SiO$_2$≤0.32
M$^+$: SiO$_2$≤0.32
SDA: SiO$_2$≤0.10
H$_2$O: SiO$_2$≤20 b) subjecting said synthesis mixture to crystallization conditions to form crystals of a mordenite zeolite comprising the structure directing agent (SDA) within its pores. The components of the synthesis mixture are combined and maintained under crystallization conditions.

Suitable sources of silicon (Si) include silica, colloidal suspensions of silica, precipitated silica, alkali metal silicates such as potassium silicate and sodium silicate, tetraalkyl orthosilicates, and fumed silicas such as Aerosil and Cabosil. Preferably, the source of Si is a precipitated silica such as Ultrasil (available from Evonik Degussa) or HiSil (available from PPG Industries).

Suitable sources of aluminum (Al) include aluminum sulfate, aluminum nitrate, aluminum hydroxide, hydrated alumina such as boehmite, gibbsite and/or pseudoboehmite, sodium aluminate and mixtures thereof. Other aluminum sources include, but are not limited to, other water-soluble aluminum salts, or an aluminum alkoxide, such as aluminum isopropyloxide, or an aluminum metal, such as aluminum in the form of chips. Preferably, the aluminum source is sodium aluminate, for example an aqueous solution of sodium aluminate with a concentration in the range of 40 to 45%, or aluminum sulfate, for example an aluminum sulfate solution with a concentration in the range of from 45 to 50%.

Alternatively or in addition to previously mentioned sources of Si and Al, aluminosilicates may also be used as a source of both Si and Al. Preferably, the Si: Ale molar ratio in the synthesis mixture is in the range of from 15 to 40, more preferably from 20 to 30.

The synthesis mixture also contains a source of alkali metal cation $M^+$. The alkali metal cation $M^+$ is preferably selected from the group consisting of sodium, potassium and mixtures of sodium and potassium cations. Sodium cation is preferred. Suitable sodium sources may be, for example, a sodium salt such as NaCl, NaBr or $NaNO_3$, sodium hydroxide or sodium aluminate, preferably sodium hydroxide or sodium aluminate. Suitable potassium sources may be, for example, potassium hydroxide or potassium halide such as KCl or KBr, or potassium nitrate. Preferably, the ratio $M^+$:Si in the synthesis mixture is in the range of from 0.15 to 0.32, more preferably from 0.20 to 0.32. Optionally, the ratio $M^+$:Si is less than 0.30.

The synthesis mixture also contains a source of hydroxide ions, for example, an alkali metal hydroxide such as sodium hydroxide or potassium hydroxide. Hydroxide can also be present as a counter ion of the structure directing agent or by the use of aluminum hydroxide as a source of Al. Preferably the range $OH^-$: Si is greater than 0.13, and may, for example, be in the range of from 0.15 to 0.32, preferably from 0.20 to 0.32. Optionally, the $OH^-$: Si ratio is less than 0.30. The synthesis mixture optionally comprises seeds. The seeds may be any suitable zeolite seed crystals, such as ZSM-5 or mordenite seed crystals. Preferably, the seeds are mesoporous mordenite crystals. The seeds may, for example, be present in an amount from 0 wt % to 10 wt %, preferably from 0.01 wt % to 10 wt % such as from 0.1 wt % to 5.0 wt % of the synthesis mixture. In a preferred embodiment, the synthesis mixture comprises seeds.

The structure directing agent, also referred to as SDA, is TEA and/or MTEA, preferably TEA, and may be present in any suitable form, for example as a halide, but is preferably present in its hydroxide form. Suitable sources of the structure directing agent include TEABr, TEAOH, MTEACl, MTEABr and MTEAOH. A preferred source of structure directing agent is TEABr. Preferably, the ratio SDA:Si is in the range of from 0.005 to 0.10, more preferably from 0.02 to 0.10, especially from 0.02 to 0.05.

The synthesis of small crystal mordenite is favored by having a relatively high solids content in the synthesis mixture. Preferably, the $H_2O$:Si ratio is no more than 20, for example, in the range of from 5 to 20, preferably from 5 to 17, especially from 10 to 17. The synthesis mixture may, for example, have a composition, expressed in terms of molar ratios, as indicated in Table 1.

Crystallization can be carried out under either static or stirred conditions in a suitable reactor vessel, such as for example, polypropylene jars or Teflon® lined or stainless steel autoclaves. Suitable crystallization conditions include a temperature of about 100° C. to about 200° C., such as about 135° C. to about 160° C. Preferably, the temperature is less than 145° C. The synthesis mixture may be held at the elevated temperature for a time sufficient for crystallization to occur at the temperature used, for example, from about 1 day to about 100 days, optionally from 1 to 50 days for example about 2 days to about 40 days. The synthesis mixture may in some cases be maintained at a first temperature for a first period of from 1 hour to 10 days and then raised to a second, higher temperature for a period of from 1 hour to 40 days. After the crystallization step, the synthesized crystals are separated from the liquid and recovered.

TABLE 1

Meso-Mordenite Synthesis Mixture

| Molar ratio | Preferred | More preferred | Especially preferred |
|---|---|---|---|
| $SiO_2$:$Al_2O_3$ | 15 to 40 | 20 to 35 | 20 to 30 |
| $OH^-$:$SiO_2$ | 0.15 to 0.32 | 0.20 to 0.32 | 0.20 to <0.30 |
| $M^+$:$SiO_2$ | 0.15 to 0.32 | 0.20 to 0.32 | 0.20 to <0.30 |
| SDA:$SiO_2$ | 0.005 to 0.10 | 0.02 to 0.10 | 0.02 to 0.05 |
| $H_2O$:$SiO_2$ | 5 to 20 | 5 to 17 | 10 to 17 |

In its as-synthesized form, the second zeolite typically has a chemical composition having the molar relationship shown in Equation (1).

$$mQ:nSiO_2:Al_2O_3 \quad (1)$$

In Equation (1), m and n are related as $0.001 \leq m/n \leq 0.1$, for example $0.001 \leq m/n \leq 0.05$. In Equation (1), n is at least 10, for instance from 10 to 60, preferably from 15 to 40, and Q is the structure directing agent.

Since the as-synthesized meso-mordenite zeolite contains the structure directing agent within its pore structure, the product is usually activated before use in such a manner that the organic part of the structure directing agent, i.e., TEA and/or MTEA, is at least partially removed from the zeolite.

The calcined meso-mordenite zeolite is optionally prepared by calcining the mordenite zeolite to remove the structure directing agent. The meso-mordenite zeolite may also be subjected to an ion-exchange step to replace the alkali or alkaline earth metal ions present in the as-synthesized product with other cations. Preferred replacing cations include metal ions, hydrogen ions, hydrogen precursor such as ammonium ions and mixtures thereof, more preferably hydrogen ions or hydrogen precursors. For instance, the meso-mordenite zeolite may be subjected to an ion-exchange step to replace the alkali or alkaline earth metal ions with ammonium cations, followed by calcination to convert the meso-mordenite zeolite in ammonium form to a meso-mordenite zeolite in hydrogen form. In one embodiment, the meso-mordenite zeolite is first subjected to a calcination step, sometimes referred to as a "pre-calcination" to remove the structure directing agent from the pores of the meso-mordenite zeolite, followed by an ion-exchange treatment, followed by a further calcination step. However, it has been found that for the meso-mordenite zeolite of the present invention, a pre-calcination step is not always required. In an alternative embodiment, the meso-mordenite zeolite is thus subjected to an ion-exchange treatment without being subjected to a prior calcination step (or pre-calcination), and, following the ion exchange treatment, is calcined to remove the structure directing agent from the pores, thereby providing the calcined meso-mordenite zeolite used in the second zeolite of this invention.

The ion-exchange step may involve, for example, contacting the meso-mordenite zeolite with an aqueous ion exchange solution. Such contact may be take place, for example, from 1 to 5 times. The contacting with the ion exchange solution is optionally at ambient temperature, or alternatively may be at an elevated temperature. For example, the meso-mordenite zeolite may be ion exchanged by contact with aqueous ammonium nitrate solution at room temperature followed by drying and calcination.

Suitable calcination conditions include heating at a temperature of at least about 300° C., preferably at least about 370° C. for at least 1 minute and generally not longer than 20 hours, for example, for a period of from 1 hour to 12 hours. While subatmospheric pressure can be employed for the thermal treatment, atmospheric pressure is desired for reasons of convenience. The thermal treatment can be performed at a temperature up to about 925° C. For instance, the thermal treatment can be conducted at a temperature of from 400° C. to 600° C., for instance from 500° C. to 550° C., in the presence of an oxygen-containing gas.

The calcined meso-mordenite zeolite typically has a Si:$Al_2$ ratio of at least 10, for example 10 to 60, more preferably 15 to 40.

The catalyst composition of this invention comprises a first zeolite corresponding to a MEL framework type zeolite (ZSM-11) and/or MFI framework type zeolite (ZSM-5), optionally having a constraint index of 3 to 12; a second zeolite comprising a meso-mordenite zeolite; a silica binder; and at least one first metal. In some embodiments, the catalyst composition can further include at least one second metal.

In some embodiments, the weight ratio of the first zeolite to the second zeolite in the catalyst can be any convenient ratio, e.g., ranging from 0.01 to 100. Preferably the weight ratio of the first zeolite to the second zeolite ranges from 0.1 to 1, such as from 0.2 to 0.8, or from 0.3 to 0.6. The first zeolite and second zeolite can be present as a mixture that is formed in any convenient manner. For example, the zeolites can be co-extruded into particles, or the zeolites can be separately extruded into particles and then mixed in a catalyst bed.

In addition to the first zeolite and the second zeolite, the catalyst comprises at least one first metal in Groups 7-10 and at least one second metal in Groups 2 and 11-15 of the periodic table. In some embodiments, the at least one first metal can correspond to a metal from Group 10 of the IUPAC Periodic Table, and at least one second metal of Group 11 to Group 15 of the IUPAC Periodic Table. For example, when the first metal corresponds to a Group 10 metal, the at least one first metal can include, but is not limited to, one or more of nickel (Ni), palladium (Pd), platinum (Pt), and compounds containing natural metals or ions thereof, preferably platinum. When the second metal corresponds to a Group 11 to 15 metal, the at least one second metal can include, but is not limited to, one or more of copper (Cu), silver (Ag), gold (Au), zinc (Zn), cadmium (Cd), gallium (Ga), indium (In), tin (Sn), bismuth (Bi), and compounds containing natural metals or ions thereof, preferably tin. In some embodiments, the at least one second metal can be selected from Mg and/or Groups 11 to 15.

In some embodiments, the catalyst composition can include 0.001 wt % to 5.0 wt % of the first metal (such as Pt, Pd, or a combination thereof), or 0.01 wt % to 1.0 wt %, or 0.02 wt % to 5.0 wt %, or 0.02 wt % to 1.0 wt %, or 0.05 wt % to 0.6 wt %. For example, the catalyst composition can include 0.005 wt % or more of Pt, or 0.02 wt % or more, or 0.05 wt % or more, or 0.10 wt % or more, such as up to 2.0 wt %, or up to 5.0 wt %, based on the weight of the catalyst composition. Additionally or alternately, in such embodiments, the catalyst composition can include 0.002 wt % to 5.0 wt % of the second metal, or 0.01 wt % to 2.0 wt %. For example, the catalyst composition can include 0.001 wt % or more of the at least one second metal, or 0.01 wt % or more, or 0.05 wt % or more, or 0.10 wt % or more, such as up to 2.0 wt %, or up to 5.0 wt %, based on the weight of the catalyst composition. Optionally but preferably, the catalyst composition can include a molar ratio of second metal to first metal of 0.5 to 10, or 1.0 to 10, or 0.5 to 7.0, or 1.0 to 7.0.

The metal component, for example, the first metal and/or the second metal, may be provided on the catalyst composition in any manner, for example, by conventional methods such as impregnation or ion exchange of the first zeolite and/or the second zeolite with a solution of a compound of the relevant metal before or after forming the catalyst particle.

It may be desirable to incorporate another material into the first zeolite and the second zeolite in the catalyst composition that is resistant to the temperatures and other conditions employed in the transalkylation process of the invention. Such materials include active and inactive materials and synthetic or naturally occurring zeolites, as well as clays and/or silica. Use of a material in conjunction with the first zeolite and the second zeolite, i.e. combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, for example bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

In various aspects, the catalyst can further include a silica binder. Any convenient type of silica binder can be used. Examples of suitable commercially available silica sources include Ultrasil® (available from Evonik) and Ludox® colloidal silica (available from W. R. Grace). For catalysts that include a binder, the binder can be incorporated into the catalyst composition in any convenient manner, such as by co-extrusion of the zeolites and binder to form particles. Each zeolite is usually admixed with the binder or matrix material so that the final catalyst composition contains the binder or matrix material in an amount ranging from 5 to 90 wt %, and typically from 10 to 60 wt %, based on the weight of the catalyst composition. For example, the binder can correspond to 5 wt % to 60 wt % of the catalyst composition, or 5 wt % to 50 wt %, or 5 wt % to 30 wt %, or 10 wt % to 30 wt %.

Prior to use, steam treatment of the catalyst composition may be employed to minimize the aromatic hydrogenation activity of the catalyst composition. In the steaming process, the catalyst composition is usually contacted with from 5% to 100% steam, at a temperature of at least 260° C. to 650° C. for at least one hour, specifically 1 to 20 hours, at a pressure of 100 to 2590 kPA-a and a WHSV of about 0.002 $hr^{-1}$ to about 20 $hr^{-1}$.

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from about 320° C. to 480° C. The source of sulfur can be contacted with the catalyst via a carrier gas, such as hydrogen or nitrogen.

After contacting the catalyst composition with the hydrocarbon feed, the catalyst may be deactivated due to coking or metal agglomeration. The deactivated catalyst can be regenerated conveniently by coke burning with a stream comprising oxygen or oxygen containing compounds, such as, ozone, oxochlorine, carbon dioxide or the like, metal re-dispersing using oxdization-reduction cycle, oxochloride treatment or the like, washing with liquid hydrocarbons or aqueous solution of inorganic and/or organic chemical compounds, such as, water, ethanol, acetone, or the like, or rejuvenation with a stream comprising hydrogen. Regeneration or rejuvenation can be performed at a temperature range from ambience to about 600° C., a pressure range of about 100 kPa-a to about 5000 kPa-a, and WHSV of about 0.2 hr$^{-1}$ to about 100 hr$^{-1}$.

Feedstock

The feedstock used in the process of the invention comprises one or more aromatic compounds containing at least 8 carbon atoms, for example, $C_8$ aromatic hydrocarbons. Specific $C_8$ aromatic hydrocarbons include ethylbenzene and dimethylbenzene isomers. Typically, such $C_{8+}$ aromatic hydrocarbons comprise aromatic compounds having a boiling point in the range of about 135 to about 230° C. at atmospheric pressure.

In some embodiments, the feedstock can include aromatic compounds having 9 or more carbon atoms, for example, $C_{9+}$ aromatic hydrocarbons. Specific $C_9+$ aromatic compounds found in a typical feed can include mesitylene (1,3,5-trimethylbenzene), durene (1,2,4,5-tetramethylbenzene), hemimellitene (1,2,4-trimethylbenzene), pseudocumene (1,2,4-trimethylbenzene), ethyltoluene, ethylxylene, 1,2-methylethylbenzene, 1,3-methylethylbenzene, 1,4-methylethylbenzene, propyl-substituted benzenes, butyl-substituted benzenes, dimethylethylbenzenes, methylpropylbenzene, methylbutylbenzene, and a mixture of two or more thereof.

Suitable sources of the $C_{9+}$ aromatics are any $C_{9+}$ fractions from any refinery process that is rich in aromatics. In some embodiments, the aromatics fraction can include a substantial proportion of $C_{9+}$ aromatics, for example, at least 80 wt % $C_{9+}$ aromatics, wherein preferably at least 80 wt %, and more preferably more than 90 wt %, of the hydrocarbons will range from $C_9$ to $C_{12}$. Typical refinery fractions which may be useful include catalytic reformate, fluidized catalytic cracking (FCC) naphtha or thermoform catalytic cracking (TCC) naphtha.

The feedstock may also comprise benzene or toluene or a mixture of benzene and toluene. Thus, in one practical embodiment, the feed to a transalkylation reactor in a transalkylation process can comprise ethylbenzene, $C_9$+ aromatics hydrocarbons and toluene. The feedstock may also include recycled/unreacted/produced benzene, toluene, ethylbenzene, and $C_9$+ aromatics that is obtained by distillation of the effluent product of the transalkylation reaction itself. Typically, toluene constitutes from about 5 wt % to about 90 wt % and $C_9$+ constitutes from about 10 to about 95 wt % of the feedstock. In a typical light feedstock, toluene constitutes from about 40 wt % to about 90 wt %, such as from 50 wt % to 70 wt % of the entire feed, whereas the $C_{9+}$ aromatics component constitutes from 10 to 60 wt %, such as from 30 to 50 wt %, of the entire feedstock to the transalkylation reaction zone. In a typical heavy feed, toluene constitutes from about 15 wt % to about 50 wt %, such as from 25 to 40 wt % of the entire feed, whereas the $C_{9+}$ aromatics component constitutes from 50 to 85 wt %, such as from 60 to 75 wt %, of the entire feed to the transalkylation reaction zone.

Hydrocarbon Conversion Process

The process for the conversion of a feedstock comprising $C_{8+}$ aromatic hydrocarbons to converted product mixture comprises the steps of contacting said feedstock and optionally hydrogen in the presence of any one of the catalyst compositions of this invention under suitable conversion conditions to produce said converted product mixture comprising, e.g., benzene, toluene and xylene.

The process can be conducted in any appropriate reactor including a radial flow, fixed bed, continuous flow or fluid bed reactor. In one alternative, the reactor for contacting said feedstock under said suitable conversion conditions comprises at least one single fixed catalyst bed of said catalyst. In another alternative, the reactor for contacting said feedstock under said suitable conversion comprises at least one moving catalyst bed of said catalyst.

The conversion conditions typically include a temperature ranging from 340° C. to 515° C., such as from 400° C. to 454° C.; a pressure from 380 to kPa-a 4240 kPa-a, such as from 1480 kPa-a to 3550 kPa-a; a hydrogen to hydrocarbon molar ratio from 1 to 5, such as from about 1 to about 3 and a WHSV of 0.2 hr$^{-1}$ to 100 hr$^{-1}$, such as from 1 hr$^{-1}$ to 100 hr$^{-1}$. The transalkylation reaction conditions are sufficient to convert the aromatic feed (especially the heavy $C_{9+}$ aromatics) to a product containing substantial quantities of $C_6$-$C_8$ aromatic compounds, such as benzene, toluene and xylenes, especially benzene and xylene. The trans alkylation reaction conditions also are sufficient to convert the ethylbenzene in the feed to benzene and ethane.

In one preferred embodiment, contacting the feedstock with the catalyst composition is effected in the presence of hydrogen fed into the reactor. The presence of hydrogen is particularly advantageous where in the conversion process, dealkylation of certain alkyl benzenes occurs to produce an olefin. It is desirable that such olefin is saturated by the hydrogen present in the reaction in a hydrogenation reaction catalyzed by the catalyst composition of this disclosure.

In a particularly advantageous embodiment of the conversion process of this disclosure, $C_{9+}$ hydrocarbons in the feed react with benzene and/or toluene in the feed in the presence of the catalyst composition to produce a converted product mixture rich in xylenes, which can be separated to produce valuable products such as para-xylene and/or ortho-xylene.

In this disclosure, a "feed" or "feedstock" is used to mean the aggregate of all materials fed into a reactor or a vessel. It should be understood to mean feeding one or multiple streams of materials into the reactor or vessel, with the same or different compositions.

EXAMPLES

The measurement of average primary particle size and primary particle size distribution was carried out as follows. Several TEM photographs of the zeolite sample were taken; primary particles were identified and measured. For each primary particle having an aspect ratio greater than 1, the longest dimension was identified by drawing a line between the two points at the edge of the particle which were the furthest apart. Then the length of the primary particle along a 45° diagonal to that longest dimension and passing through the mid-point of that longest dimension was measured as the particle size. Each measurement was grouped by being assigned to one of about 10 particle size ranges covering the range of sizes found in the sample. For example, size ranges centered around 187.5, 250, 312.5, 375, 437.5, 500, 562.5 and 625 Angstroms could be used. The percent (%) crystals value on the y-axis was calculated from: Number of particles in each group/total number of particles measured multiplied by 100. The average particle size was calculated as the arithmetical mean based on the grouped results.

The total BET and the t-Plot micropore surface area were measured by nitrogen adsorption/desorption with a Micromeritics Tristar II 3020 instrument after degassing of the calcined zeolite powders for 4 hrs at 350° C. The mesopore surface area was obtained by the subtraction of the t-plot micropore from the total BET surface area. The mesopore volume was derived from the same data set. More information regarding the method can be found, for example, in "Characterization of Porous Solids and Powders: Surface Area, Pore Size and Density", S. Lowell et al., Springer, 2004.

The X-ray diffraction data (powder XRD or XRD) were collected with a Bruker D4 Endeavor diffraction system with a VANTEC multichannel detector using copper K-alpha radiation. The diffraction data were recorded by scanning mode with 0.018 degrees two-theta, where theta is the Bragg angle, and using an effective counting time of about 30 seconds for each step.

The crystal sizes in the a, b and c crystal vectors were calculated based on the three (200), (020) and (002) peaks in the X-ray diffraction patterns using the Scherrer equation (P. Scherrer, N. G. W. Gottingen, Math-Pys., 2, p. 96-100 (1918)). The method and its application to zeolites are also described in A. W. Burton, K. Ong, T. Rea, I. Y. Chan, Microporous and Mesoporous Materials, 117, p. 75-90 (2009). For the measurements described herein the Jade version 9.5.1 X-ray diffraction analysis software by Materials Data, Inc., was used to perform the calculation.

The Alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Example 1—Preparation of Meso-Mordenite Crystals

A mixture was prepared from using water, TEABr (50% solution), Ultrasil silica, sodium aluminate solution (45%), and 50% sodium hydroxide solution. Mordenite seeds were then added to the mixture. The mixture had the following molar composition:
$SiO_2/Al_2O_3$~26.10
$H_2O/SiO_2$~15.11
$OH^-/SiO_2$~0.291
$Na^+/SiO_2$~0.291
Template/$SiO_2$~0.049

The mixture was reacted at 290° F. (145° C.) with stirring at 350 RPM for 72 hours. The product was filtered, washed with deionized (DI) water and dried at 250° F. (120° C.). The XRD pattern of the as-synthesized material showed the typical pure phase of Mordenite topology. The SEM of the as-synthesized material showed morphology of irregularly-shaped aggregates composed of small crystallites. The as-synthesized crystals were pre-calcined in nitrogen at 540° C. and then converted into the hydrogen form by three ion exchanges with ammonium nitrate solution at room temperature, followed by drying at 250° F. (120° C.) and calcination at 1000° F. (540° C.) for 6 hours. The resulting mordenite crystals had a $SiO_2/Al_2O_3$ molar ratio of ~21, surface area of 637 m$^2$/g and meso-pore surface area of 56 m$^2$/g, Hexane sorption of 53.3 mg/g and an Alpha value of 1200.

Examples 2 to 4: Synthesis of ZSM-11 Crystals

Mixtures were prepared from water, TBABr (50% solution), Ultrasil™ silica, aluminum sulfate solution (47%), 50% sodium hydroxide solution, and ZSM-11 seeds. The compositions of the three types of synthesis mixtures are shown in Table 2. Table 2 also shows the initial mixing and stirring conditions.

TABLE 2

ZSM-11 Synthesis Mixtures

| | Example 2 | Example 3 | Example 4 |
|---|---|---|---|
| Si/Al$_2$ molar ratio in crystal | ~45:1 | ~90:1 | ~27:1 |
| Molar ratios in synthesis mixture for making crystal | SiO$_2$/Al$_2$O$_3$~50.2 H$_2$O/SiO$_2$~13.9 OH$^-$/SiO$_2$~0.15 Na$^+$/SiO$_2$~0.26 Template/SiO$_2$~0.06 | SiO$_2$/Al$_2$O$_3$~100 H$_2$O/SiO$_2$~18.4 OH$^-$/SiO$_2$~0.14 Na$^+$/SiO$_2$~0.19 Template/SiO$_2$~0.05 | SiO$_2$/Al$_2$O$_3$~28.3 H$_2$O/SiO$_2$~13.6 OH$^-$/SiO$_2$~0.10 Na$^+$/SiO$_2$~0.31 Template/SiO$_2$~0.08 |
| Reaction conditions for making crystal | Reacted at 121° C./350 RPM for 72 hours, then 138° C./350 rpm for 48 hrs | Reacted at 143° C./250 RPM for 48 hours | Reacted at 121° C./250 RPM for 48 hours, then 138° C./250 RPM for 24 hours |

The products were then filtered, washed with deionized (DI) water, and dried at 250° F. (120° C.). The XRD patterns for each of the resulting crystals (i.e., the as-synthesized material) showed the typical pure phase of ZSM-11 topology. The SEM of the as-synthesized material showed morphology of agglomerates composed of small crystallites with size of <0.05 micron. The as-synthesized crystals were converted into the hydrogen form by three ion exchanges with ammonium nitrate solution at room temperature, followed by drying at 250° F. (120° C.) and calcination at 1000° F. (540° C.) for 6 hours. The crystals from Example 2 had a total surface area (SA) (i.e., micropore SA+mesopore SA) of 481 m$^2$/g, and a hexane sorption of 96.9 mg/g. The crystals from Example 4 had a total surface area (SA) (i.e., micropore SA+mesopore SA) of 484 m$^2$/g, and a hexane sorption of 98.2 mg/g.

Example 5 (Comparative)—Synthesis of ZSM-5 Crystals

A mixture was prepared from water, TPABr (35% solution), HiSil™ silica, 45% Sodium aluminate solution, 50% sodium hydroxide solution, and ZSM-5 seeds. The mixture had the following molar composition:
$SiO_2/Al_2O_3$~61
$H_2O/SiO_2$~11
$OH^-/SiO_2$~0.18
$Na^+/SiO_2$~0.18
Template/$SiO_2$~0.05

The mixture was reacted at temperatures from 100° C. to 150° C. with stirring. The product was filtered, washed with deionized (DI) water and dried at 250° F. (120° C.). The XRD pattern of the as-synthesized material showed the typical pure phase of ZSM-5 topology. The SEM of the as-synthesized material showed morphology of agglomerates composed of small crystallites with size of <0.1 micron. The as-synthesized crystals were pre-calcined in nitrogen at 540° C. and then converted into the hydrogen form by three ion exchanges with ammonium nitrate solution at room temperature, followed by drying at 250° F. (120° C.) and calcination at 1000° F. (540° C.) for 6 hours. The resulting ZSM-5 crystals had a $SiO_2/Al_2O_3$ molar ratio of ~50, a total surface area (SA) of 480 m²/g, and a hexane sorption of ~100 mg/g.

Example 6 (Comparative)—0.30 wt % Pt/3× Ga on 50 wt % Meso-Mordenite/20 wt % ZSM-5/30 wt % Alumina 50 parts of Meso-Mordenite crystals from Example #1 were mixed with 20 parts of ZSM-5 crystals from example 5 and 30 parts alumina (Versal 300) in a muller. An aqueous solution of Tetraammineplatinum chloride and Gallium (III) Nitrate in water was added to the muller prior to forming to a target loading on the final extrudates of 0.03 wt % Pt and 0.032 wt % Ga. Sufficient water was added to produce an extrudable paste on an extruder, ranging from 49-53% total solids. The mixture was extruded into ¹⁄₁₆" cylinder and then dried on a conveyor convection oven at 121° C. for several hours. The dried extrudates was precalcined in nitrogen at 538° C. to decompose and remove the organic template. The precalcined extrudates were then humidified with saturated air at ambient conditions for an hour at 2 cc/g/min. After humidification, the extrudates were exchanged with 1 N ammonium nitrate to remove sodium. The extrudates were then washed with deionized water to remove residual nitrate ions prior to drying at 121° C. for at least 4 hours, followed by calcination in air at 538° C.

Examples 7-14: Preparation of Meso-Mordenite/ZSM-11/Silica Binder

A series of catalysts including Meso-Mordenite, ZSM-11, silica binder, Pt, and Sn were prepared using the following procedure (Examples 8-14). Additionally, a comparative example using an alumina binder instead of a silica binder was prepared in a similar manner (Example 7). The amounts of each component in the resulting catalyst are shown in Table 3 below. The relative molar amount of Sn versus Pt is also shown.

Meso-mordenite crystals from Example 1 were mixed with ZSM-11 crystals and silica as a binder (or alumina for Example 7) in a muller. Most of the mixtures included the ZSM-11 crystals from Example 2, which had a $Si/Al_2$ ratio of ~45. The exception is Example 8, where the ZSM-11 from Example 4 was used ($Si/Al_2$ ratio~27). The alumina binder was Versal 300. The silica binder was a commercially available Ultrasil silica, with the exception of Example 14, where a combination of Ultrasil and Ludox silica was used. An aqueous solution of Tetraammineplatinum chloride and Tin(II) chloride dehydrate in water was added to the muller to achieve a desired target loading prior to forming the final extrudates of Pt and Sn. Sufficient water was added to produce an extrudable paste on a 1" extruder, ranging from 49-53% total solids. The mixture of EMM-34, ZSM-11, alumina, and water was extruded into ¹⁄₁₆" cylinder and then dried in a hotpack oven at 121° C. overnight. The dried extrudates were precalcined in nitrogen at 538° C. to decompose and remove the organic template. The precalcined extrudates were then humidified with saturated air at ambient conditions for an hour at 2 cc/g/min. After humidification, the extrudates were exchanged with 1 N ammonium nitrate to remove sodium. The extrudates were then washed with deionized water to remove residual nitrate ions prior to drying at 121° C. for at least 4 hours, followed by calcining in air at 538° C.

TABLE 3

Compositions for Examples 7-14

| Example No. | Meso-Mordenite (wt %) | ZSM-11 (wt %) | Binder (wt %) | Pt (wt %) | Sn (wt %) | Sn/Pt molar ratio |
|---|---|---|---|---|---|---|
| 7 | 44 | 36 | 20 (Alumina) | 0.03 | 0.11 | 6 |
| 8 | 50 | 20 ($Si/Al_2$ ratio ~27) | 30 | 0.026 | 0.096 | 6 |
| 9 | 44 | 36 | 20 | 0.03 | 0.11 | 6 |
| 10 | 50 | 20 | 30 | 0.03 | 0.11 | 6 |
| 11 | 44 | 36 | 20 | 0.015 | 0.055 | 6 |
| 12 | 44 | 36 | 20 | 0.022 | 0.080 | 6 |
| 13 | 40 | 16 | 44 | 0.021 | 0.077 | 6 |
| 14 | 44 | 36 | 20 (mixed silica) | 0.03 | 0.11 | 6 |

Example 15—Aromatic Conversion Results

The catalysts in Examples 6-14 were tested in a laboratory scale fixed bed unit using a feed corresponding to 60 wt % of a $C_{9+}$ heavy aromatic raffinate and 40 wt % toluene. For each example, the extrudate was sized to 14-18 mesh (1000-1410 μm) and loaded into the reactor with equal parts quartz. The catalysts were activated by heating in hydrogen to 400° C. and held at that temperature for 2 hours. The catalysts were then cooled to 350° C., and then the feed blend was introduced.

The catalyst was contacted with the feedstock at a temperature of 350° C., a pressure of 390 psig (~2.7 MPa-g), and a weight hourly space velocity of 3.0 hr⁻¹ to generate results. Temperature excursions to temperatures of as high as 400° C. were periodically used in the presence of the feed in order to simulate catalyst aging.

Table 4 summarizes the results for several of the catalysts, as indicated by the Example number. The results in Table 4 include $C_{9+}$ conversion, and xylene yield. Aging rates for the catalyst activity for both $C_{9+}$ conversion and xylene yield are also provided. For the results in Table 4, the results are reported as index or normalized values in comparison with the results obtained for Example 7 (alumina-bound catalyst). Thus, $C_{9+}$ conversion, xylene yield, and the aging rates for Example 7 are normalized to either 1.0 or 0 (for the aging rates). It is noted that for the aging rates, a negative value represents less aging of the catalyst, so that a negative value means the catalyst is retaining more of the indicated activity over time.

Table 4 demonstrates a variety of results. First, with the exception of Example 11, the various combinations of meso-mordenite and ZSM-11 with various ratios of Pt and Sn appear to provide substantial catalyst lifetime advantages while providing similar $C_{9+}$ conversion, and similar or better xylene yield. Example 1 is notable for having a decreased amount of metal on the catalyst. Thus, catalyst compositions include 0.02 wt % or more of Pt (or another first metal) are preferable for providing improved resistance to aging while also providing desirable activity.

TABLE 4

C$_{9+}$ Conversion, Xylene Yield, and Aging Rates

| Example No. | Relative C$_{9+}$ Conversion | Relative C$_{9+}$ Conversion Aging Rate | Relative Xylene Yield | Relative Xylene Yield Aging Rate |
|---|---|---|---|---|
| 6 (Comparative) | 0.84 | +52.5% | 0.92 | +52.2% |
| 7 | 1.0 | +0.0 | 1.0 | +0.0 |
| 9 | 0.92 | −9.2 | 1 | −11.2 |
| 11 | 0.90 | 42.2 | 0.99 | 61.8 |
| 10 | 0.96 | −52.3 | 1.03 | −72 |
| 8 | 0.97 | −34.6 | 1.02 | −50.1 |

Figure 2:
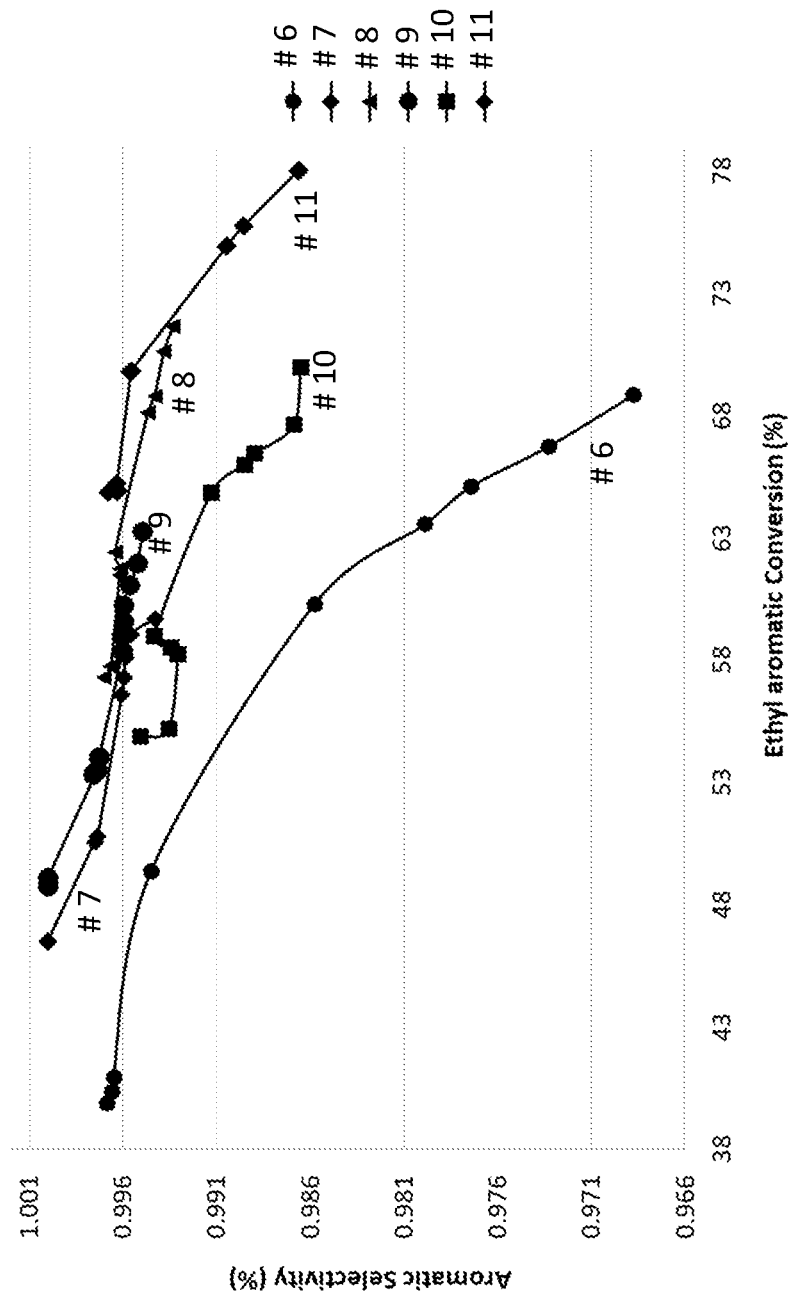
FIG. 2 shows aromatic selectivity relative to ethyl aromatics conversion for various catalysts.

Table 4 shows that catalyst compositions including a silica binder resulted in decreased catalyst aging. FIG. 2 shows aromatic selectivity versus conversion of ethyl-substituted aromatics for various catalysts from Table 4. In FIG. 2, trend lines toward the upper right corner of the figure correspond to trend lines for catalysts with favorable combinations of aromatic selectivity and conversion of ethyl-substituted aromatics. As shown in FIG. 2, the silica-bound catalysts generally provide improved aromatics selectivity relative to (comparative) Example 6, while providing roughly comparable aromatic selectivity relative to Example 7. Although the aromatics selectivity may be lower than the alumina bound catalyst, the substantial and unexpected decrease in aging rate for the silica bound catalysts in Table 4 can reduce or minimize the need to increase the severity of operating conditions over time. This can allow for a corresponding increase in run length.

Example 16—Additional Aging Rate Evaluation

Additional testing was performed on the catalysts from Examples 6, 7, and 9 to further investigate differences in activity between start of run and after the initial exposure. In the additional testing, roughly 50 g of catalyst was exposed in an adiabatic reactor to the feed from Example 15 corresponding to 60 wt % of a C$_{9+}$ heavy aromatic raffinate and 40 wt % toluene. The conditions in the additional testing were similar to the conditions for Example 15.

It is noted that the catalyst from Example 6 was pre-sulfided prior to exposure to oil. By contrast, the catalysts from Example 7 and Example 9 did not need an extra pre-sulfiding step to meet the start of the run activity and selectivity. All three catalysts were operated at isoconversion, targeting 47% (±2%) C$_9^+$ conversion and maintaining that conversion through increasing the reactor inlet temperatures. The relative changes in the required inlet temperatures to maintain this target conversion gives a direct indication of the aging rate of these catalysts.

Figure 3:
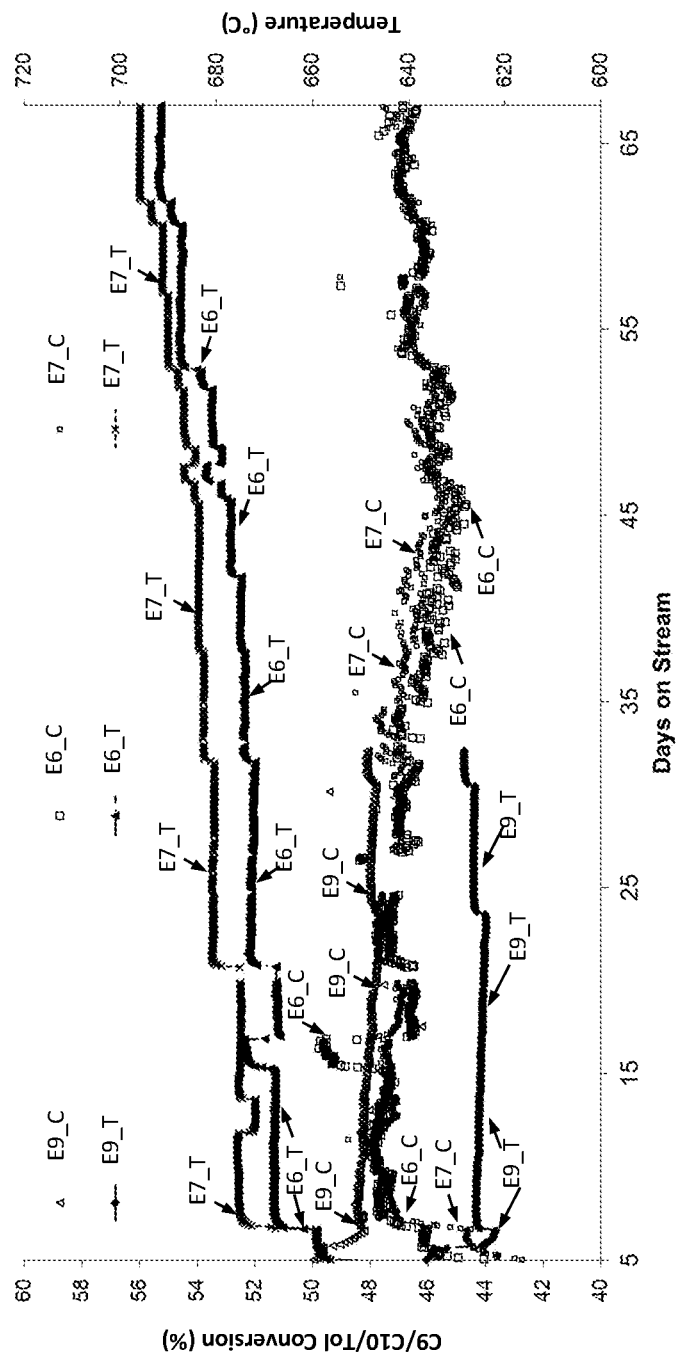
FIG. 3 shows catalyst aging rate during a transalkylation process for various catalysts.

FIG. 3 shows the impact of catalyst aging on C$_{9+}$ conversion for the catalysts from Examples 6, 7, and 9. In FIG. 3, the left axis corresponds to the amount of conversion. The right axis corresponds to the temperature in the test conditions. The bottom axis corresponds to the number of days of testing. E6_C and E6_T correspond to Example 6 conversion and Example 6 inlet temperature, respectively. E7_C and E7_T correspond to Example 7 conversion and Example 7 inlet temperature, respectively. E9_C and E9_T correspond to Example 9 conversion and Example 9 inlet temperature, respectively.

Figure 4:
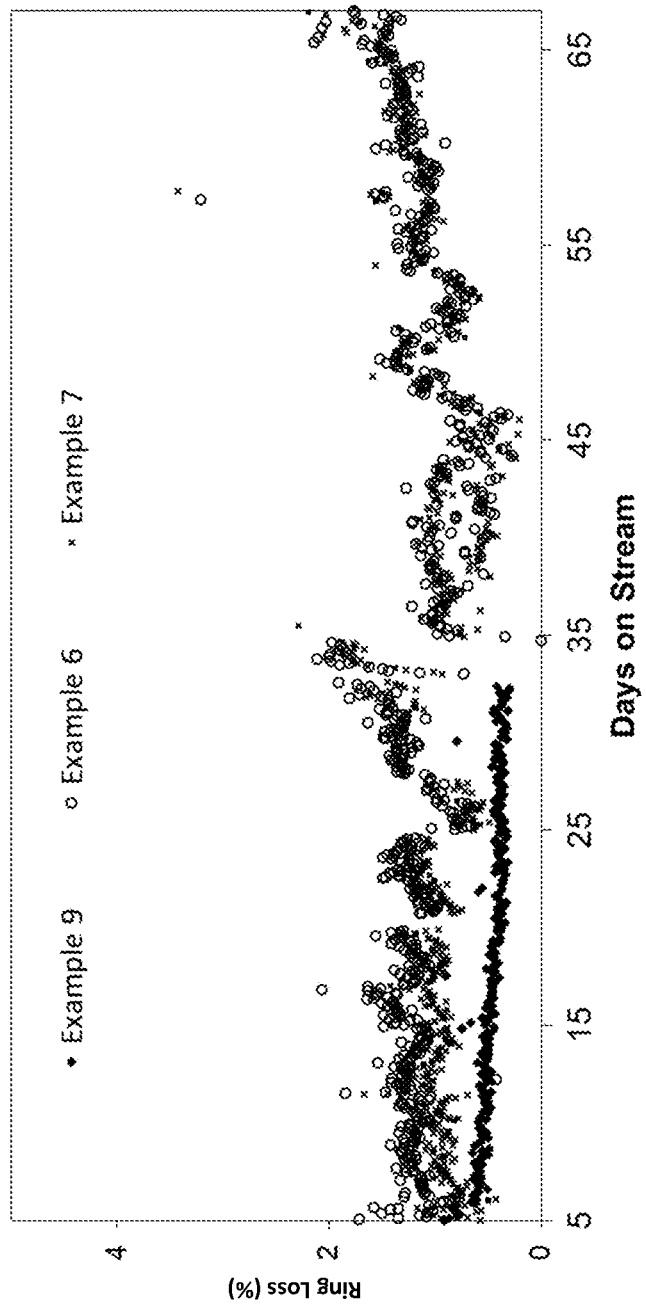
FIG. 4 shows the weight percentage of ring loss during a transalkylation process for various catalysts.

As can be seen in FIG. 3, the catalyst from Example 7 required a lower temperature rise (0.35° F./Day or 0.20° C./Day) in comparison to the comparative catalyst from Example 6 (0.41° F./Day or 0.23° C./Day). The catalyst from Example 9 showed a significantly and unexpectedly lower aging rate (0.11° F./Day or 0.06° C./Day) relative to the catalyst from both Example 6 and Example 7. The catalyst from Example 9 also offered enhanced selectivity/hydrogenation function and hence lower ring loss, as shown in FIG. 4. As shown in FIG. 4, the catalyst of Example 9 exhibited less than 0.5 wt % ring loss compared to 1.0 wt % to 1.5 wt % ring loss for the catalysts of Example 6 or Example 7.

It is worth noting that the start-up oil-in exotherms were lower for both the Example 7 and Example 9 catalysts relative to the comparative catalyst in Example 6. Larger exotherms can cause off-spec product quality at start-of-run as well as potential irreversible damage to catalyst (affecting its aging and selectivity). Additionally, as can be observed in FIG. 3, the SOR (start of the run) temperature to achieve similar levels of conversion is substantially lower for the Si-bound sample compared to Example 6 or Example 7. This indicates that Example 9 is a higher activity catalyst. The higher activity combined with slower aging rate, provides a wider temperature window to work with and results in superior cycle life.

All numerical values within the detailed description and the claims herein are modified by "about" or "approximately" the indicated value, and take into account experimental error and variations that would be expected by a person having ordinary skill in the art.

While the present invention has been described and illustrated with respect to certain embodiments, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed form any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:
1. A method for converting a feedstock comprising C$_{8+}$ aromatics, comprising:
   contacting the feedstock and optionally hydrogen with a catalyst composition under conversion conditions in a reactor comprising at least one fixed catalyst bed of the catalyst composition to produce a converted product mixture,
   wherein the catalyst composition comprises:
   (i) a zeolite mixture comprising ZSM-11, and ZSM-5, wherein a SiO$_2$/Al$_2$O$_3$ molar ratio of the ZSM-5 is greater than or equal to 21:1, wherein a weight ratio of the ZSM-11 and the ZSM-5 is 0.3 to 0.6;
   (ii) a combination of a first metal in Groups 7-10 and a second metal in Groups 2, and 11 to 15 in the Periodic Table of Elements; and
   (iii) a silica binder, wherein the silica binder comprises a mixed silica.
2. The method of claim 1, wherein the ZSM-5 has a mesopore surface area of greater than 30 m$^2$/g.

3. The method of claim 1, wherein a weight ratio of the ZSM-11 and the ZSM-5 is 0.36 to 0.44.

4. The method of claim 1, wherein the first metal comprises Ni, Pd, Pt, or a combination of two or more thereof.

5. The method of claim 1, wherein the catalyst composition comprises 0.005 wt % to 0.1 wt % Pt, based on the total weight of the catalyst composition.

6. The method of claim 1, wherein the catalyst composition comprises 0.02 wt % to 0.1 wt % of the first metal, based on the total weight of the catalyst composition.

7. The method of claim 1, wherein the second metal comprises Sn, Mg, Ga, Re, Ag, Cu, or a combination of two or more thereof.

8. The method of claim 1, wherein the catalyst composition comprises from 10 wt % to 90 wt % of the silica binder, based on the total weight of the catalyst composition.

9. The method of claim 1, wherein the catalyst composition comprises from 20 to 80 wt % of the silica binder, based on the total weight of the catalyst composition.

10. The method of claim 1, wherein feedstock comprises $C_{9+}$ aromatics and at least one of benzene and toluene, and the converted product mixture comprises xylenes.

11. The method of claim 1, wherein contacting the feedstock with the catalyst composition is effected in the presence of hydrogen.

12. The method of claim 1, wherein the conversion conditions comprise a temperature of 340° C. to 515° C., a pressure from 380 kPa-a (55 psia) to 4240 kPa-a (615 psia) and a weight hourly space velocity (WHSV) in the range of 1 to 100 $hr^{-1}$ based on the weight of the feedstock.

13. The method of claim 1, wherein the first metal is Pt and wherein the second metal is Sn.

14. The method of claim 13, wherein a molar ratio of the second metal to the first metal is 1.0 to 7.0.

15. The method of claim 13, wherein a molar ratio of the second metal to the first metal is 6.0.

16. A catalyst composition, comprising:
 (i) a zeolite mixture comprising ZSM-11, and ZSM-5, wherein a $SiO_2/Al_2O_3$ molar ratio of the ZSM-5 is greater than or equal to 21:1, wherein a weight ratio of the ZSM-11 and the ZSM-5 is 0.3 to 0.6;
 (ii) a combination of a first metal in Groups 7-10 and a second metal in Groups 2, and 11 to 15 in the Periodic Table of Elements; and
 (iii) a silica binder, wherein the silica binder comprises a mixed silica.

17. The catalyst composition of claim 16, wherein the ZSM-5 has a mesopore surface area of greater than 30 $m^2/g$.

18. The catalyst composition of claim 16, wherein the weight ratio of the ZSM-11 to the ZSM-5 is from 0.1 to 1.0.

19. The catalyst composition of claim 16, wherein the first metal comprises Ni, Pt, Pd, or a combination of two or more thereof.

20. The catalyst composition of claim 16, comprising 0.005 wt % to 0.1 wt % Pt, based on the total weight of the catalyst composition.

21. The catalyst composition of claim 16, comprising from 0.02 wt % to 0.1 wt % of Pt, based on the total weight of the catalyst composition.

22. The catalyst composition of claim 16, wherein the second metal comprises Sn, Mg, Ga, Re, Ag, Cu, or a combination of two or more thereof.

23. The catalyst composition of claim 16, comprising from 10 wt % to 90 wt % of the silica binder, based on the total weight of the catalyst composition.

24. The catalyst composition of claim 16, comprising from 20 to 80 wt % of the silica binder, based on the total weight of the catalyst composition.

* * * * *